United States Patent
Nakamura

(10) Patent No.: US 7,472,872 B2
(45) Date of Patent: Jan. 6, 2009

(54) WEIGHT BALANCING MECHANISM FOR OPERATION MICROSCOPE STAND

(75) Inventor: Katsushige Nakamura, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 816 days.

(21) Appl. No.: 11/113,004

(22) Filed: Apr. 25, 2005

(65) Prior Publication Data

US 2005/0247831 A1    Nov. 10, 2005

(30) Foreign Application Priority Data

Apr. 27, 2004    (JP)    ............... 2004-131790

(51) Int. Cl.
  *A47F 7/00*    (2006.01)
(52) U.S. Cl. ............... 248/123.2; 248/280.11
(58) Field of Classification Search ............ 248/123.2, 248/123.11, 280.11, 281.11; 359/382, 384, 359/368
  See application file for complete search history.

(56) References Cited

U.S. PATENT DOCUMENTS

| 4,867,405 | A |   | 9/1989  | Nakamura |
| 4,881,709 | A |   | 11/1989 | Nakamura |
| 5,480,114 | A |   | 1/1996  | Nakamura |
| 5,528,417 | A |   | 6/1996  | Nakamura |
| 5,651,718 | A | * | 7/1997  | Nakamura ............... 248/123.2 |
| 5,713,545 | A |   | 2/1998  | Nakamura |
| 5,812,301 | A | * | 9/1998  | Nakamura .................. 359/384 |
| 6,045,104 | A |   | 4/2000  | Nakamura et al. |
| 6,050,530 | A | * | 4/2000  | Nakamura ............... 248/123.2 |
| 2002/0108874 | A1 |   | 8/2002  | Metelski |

FOREIGN PATENT DOCUMENTS

DE    43 20 443 A1    12/1994

OTHER PUBLICATIONS

European Search Report mailed on Aug. 4, 2005.

* cited by examiner

*Primary Examiner*—Gwendolyn Baxter
(74) *Attorney, Agent, or Firm*—Cheng Law Group PLLC

(57) ABSTRACT

A first switch for performing both a weight balancing operation for a main parallel linkage and a weight balancing operation for a supplemental parallel linkage is provided separately from a second switch for only performing a weight balancing operation for the supplemental parallel linkage. An operator can press the second switch during surgery to only correct a slightly unbalanced state of the supplemental parallel linkage in a short period of time, resulting in increased operability of the operation microscope. While the first switch is provided on an operating panel at a stand body, the second switch is provided at a lower part of a distal link located above an operating space for the operation microscope. It is thus easy for an operator to press the second switch during surgery.

11 Claims, 8 Drawing Sheets

WEIGHT BALANCING MECHANISM FOR OPERATION MICROSCOPE STAND

BACKGROUND OF THE INVENTION

1. Field of the Invention

This invention relates to weight balancing mechanisms for a stand supporting an operation microscope.

2. Description of the Related Art

An operation microscope stand is known as a structure in which a main parallel linkage is rotatably supported on a rotation axis provided on a stand body which is installed on the floor or the ceiling; an operation microscope is supported via a supplemental parallel linkage at a distal end of a support arm which is an extension of the upper link of the main parallel linkage; and a counterweight is supported at an extension of the lower link of the first parallel linkage.

This operation microscope stand allows the main parallel linkage to be held at a desired position by bringing the mass center of the main parallel linkage and all the structures it supports in agreement with the rotation axis, using the counterweight for weight balancing on the rotation axis.

The operation microscope held at the distal end of the support arm via the supplemental parallel linkage can also be held at different angles by inclining the supplemental parallel linkage, for example.

This kind of operation microscope stand includes a weight balancing switch generally provided on an operating panel located at the stand body. After fitting the operation microscope and accessories to the supplemental parallel linkage, an operator presses the weight balancing switch provided on the operating panel. A weight balancing operation about the rotation axis for the main parallel linkage and a weight balancing operation for the operation microscope held by the supplemental parallel linkage are started for weight equilibrium of the main parallel linkage and the supplemental parallel linkage.

As a result, the operation microscope is held in the air as if it is floating in a zero-gravity space. Its weight equilibrium being attained in every direction, the operation microscope is kept at a desired position to which it has been moved or rotated.

In this related art, however, since both the weight balancing operation for the main parallel linkage and the weight balancing operation for the supplemental parallel linkage are performed by pressing the weight balancing switch provided on the operating panel, an operator, when he or she only wants to correct a slightly unbalanced state of the supplemental parallel linkage in a short period of time during surgery, has to perform an overall weight balancing operation, resulting in a complicated operation. More specifically, when an operator, during surgery, moves a part of the operation microscope supported by the supplemental parallel linkage relative to a supported part of the operation microscope, the form (the distribution of mass) of the operation microscope changes and its mass center shifts. Thus, the full weight equilibrium of the supplemental parallel linkage is disrupted. In this case also, an overall weight balancing operation is performed, taking time in adjustment, and preventing a prompt procedure.

SUMMARY OF THE INVENTION

The present invention has been made in view of the above problem in the related art, and provides a weight balancing mechanism for an operation microscope stand which allows for an independent weight balancing operation for a supplemental parallel linkage during surgery.

According to a first technical aspect of the present invention, there is provided a weight balancing mechanism for an operation microscope stand, which comprises a first parallel linkage supported on a first rotation axis which is fixed in position to a stand body; a distal link supported on a second rotation axis which is fixed in position to a first horizontal link element of the first parallel linkage; a second parallel linkage supported on a third rotation axis which is fixed in position to the distal link, an operation microscope being suspended from and supported by the third rotation axis via the second parallel linkage; a counterweight fixed in position to a second horizontal link element of the first parallel linkage, on the side opposite to the distal link with respect to the first rotation axis; a first control mechanism for producing a first weight balance about the first rotation axis for the first parallel linkage, using the counterweight; a second control mechanism for producing a second weight balance about the third rotation axis for the second parallel linkage; a first switch for controlling operation of the first control mechanism and the second control mechanism; and a second switch for only controlling operation of the second control mechanism. The second parallel linkage defines an operating space, and the second switch is located above the operating space.

According to a second technical aspect of the present invention, the second parallel linkage in the weight balancing mechanism comprises a main parallel linkage and an auxiliary parallel linkage, the main parallel linkage and the auxiliary parallel linkage being articulated to each other, having link elements parallel to each another. The auxiliary parallel linkage is fixed in position to the distal link via articulations which are fixed in position to a link element thereof, the articulations being provided with a first cam mechanism controlled by the second control mechanism. The operation microscope is fixed in position via a second cam mechanism controlled by the second control mechanism to a horizontal link element of the main parallel linkage which is not parallel to the link element fixed at the distal link. The counterweight can be moved to a position to produce the first weight balance by the first control mechanism. The second control mechanism controls correspondingly to an operation of the second switch so that the mass center of the operation microscope and the second parallel linkage suspended from and supported by the distal link is located substantially vertically below the third rotation axis.

DESCRIPTION OF THE PREFERRED EMBODIMENTS

Figure 1:
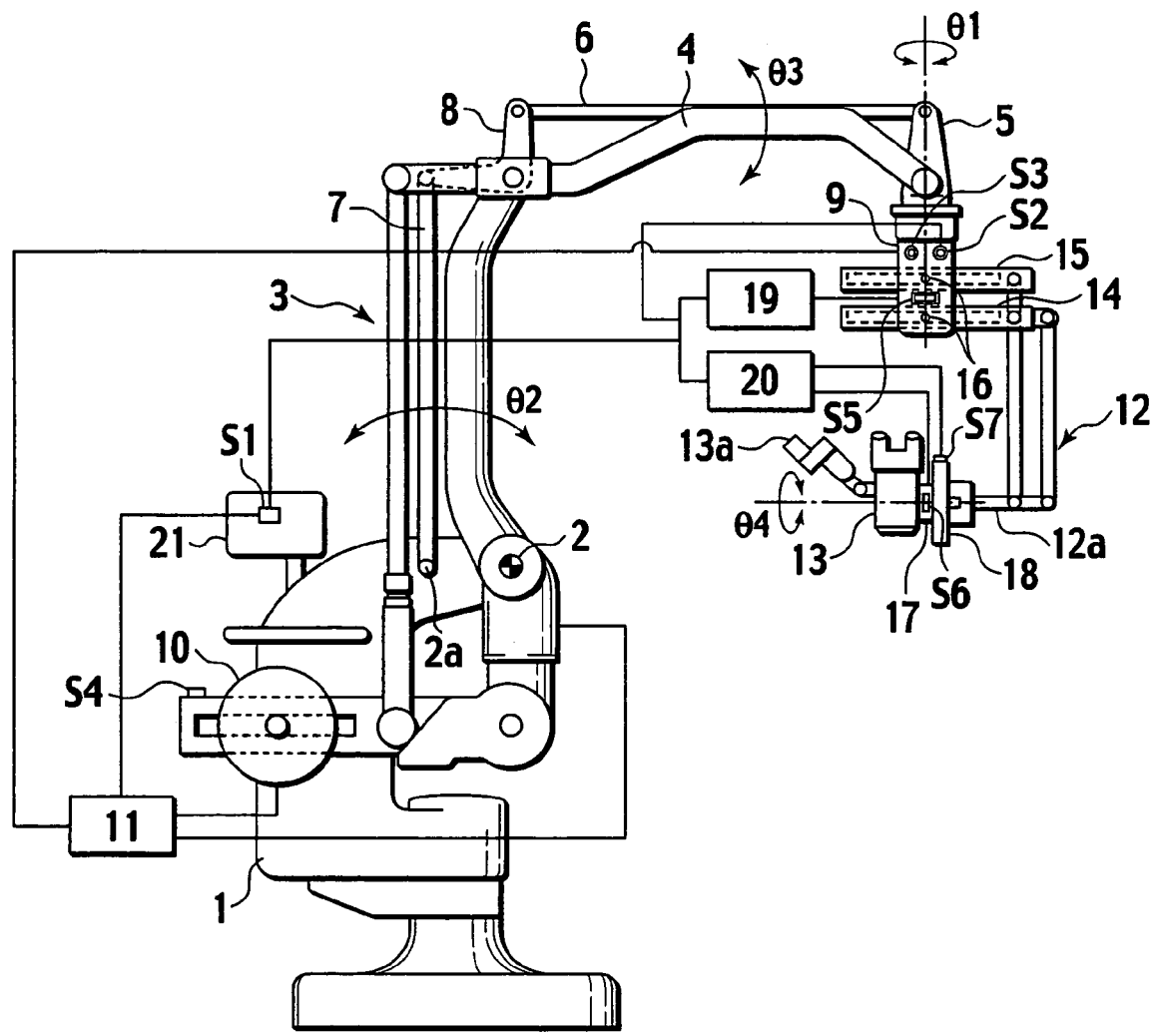
FIG. 1 is a side view of an operation microscope stand.

A preferred embodiment of the present invention will be described with reference to FIGS. 1 to 14. A stand body 1 is installed on the floor in an operating room. A rotation axis 2 is fixed relative to the stand body 1 and positions parallel to a horizontal plane. A main parallel linkage 3 (see a shaded portion in FIG. 2) is rotatably supported on the rotation axis 2 at its vertically intermediate portion.

The main parallel linkage 3 includes four link elements 3a, 3b, 3c and 3d. The link element 3b constituting the upper link is extended to form a support arm 4. A distal link 5 is provided via a rotation axis 34 at the distal end of the support arm 4 which is relatively fixed to the upper link 3b. The rotation axis 34 always positions parallel to a horizontal plane. The distal link 5 is connected at its upper end to the stand body 1 via two sub-arms 6 and 7 and an L-shaped crank lever 8. Thus, another parallel linkage with a link element 2-2a being fixed to the stand body 1 is formed, which keeps the distal link 5 substantially plumb in its longitudinal direction. The lower part of the distal link 5 is a slide drive 9 containing a motor. The slide drive 9 is part of the distal link 5, and is rotatable relative to the upper part of the distal link 5 in θ1 directions about its longitudinal direction.

Figure 3:
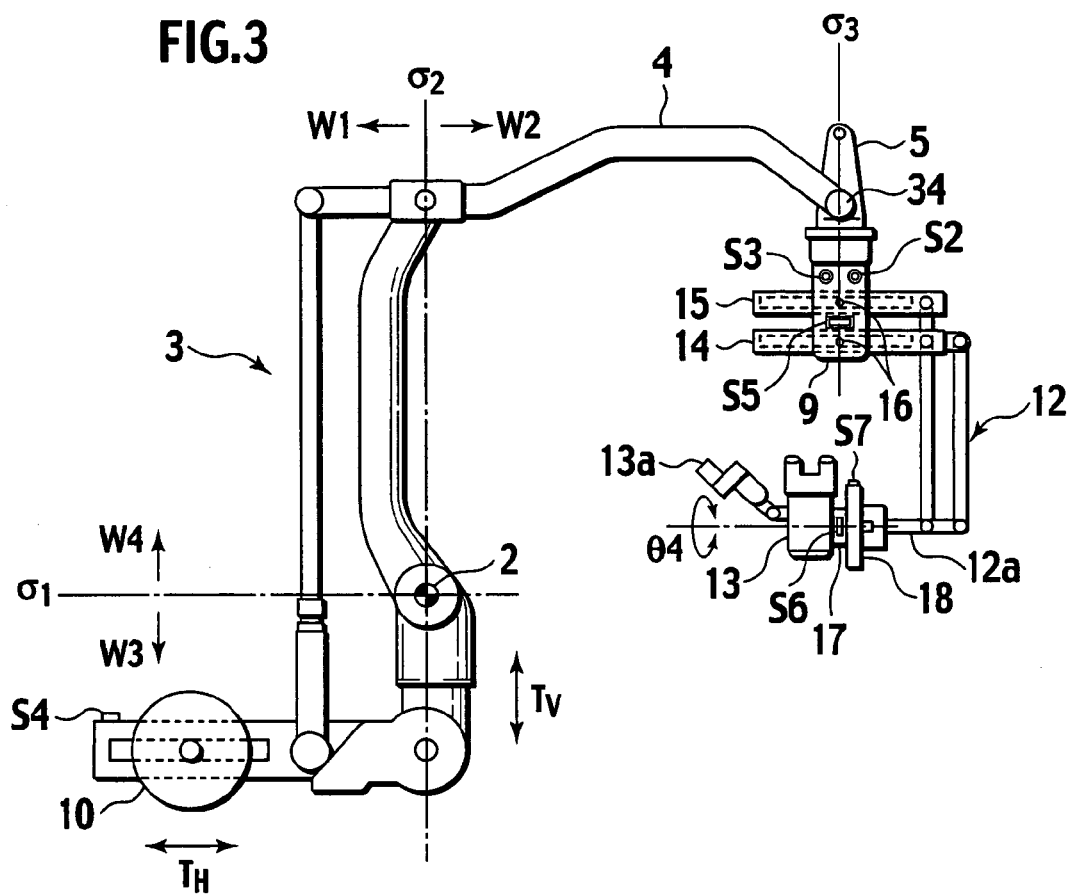
FIG. 3 is a side view illustrating the weight balance of a main parallel linkage.

A counterweight 10 is provided at an extension of the link element 3a constituting the lower link of the main parallel linkage 3, at a position opposite to the distal link 5 with respect to the rotation axis 2 of the main parallel linkage 3. The counterweight 10 can be moved in horizontal and vertical directions by a counterweight movement control means 11 to be balanced in weight with a load suspended from the distal link 5, thereby to prevent the main parallel linkage 3 from rotating about the rotation axis 2 despite the intention of the operator (first weight balance). Specifically, as shown in FIG. 3, weight W1 on the left side on the sheet plane of an imaginary vertical plane $\sigma_2$ passing through the rotation axis 2 is balanced with weight W2 on the right side on the sheet plane ($T_V$), and weight W3 on the lower side on the sheet plane of an imaginary horizontal plane $\sigma_1$ passing through the rotation axis 2 and intersecting the plane $\sigma_2$ is balanced with weight W4 on the upper side on the sheet plane ($T_H$). Even when the main parallel linkage 3 is rotated in a θ2 direction about the rotation axis 2 and the support arm 4 is rotated in a θ3 direction, they are kept at optional positions to which they have been rotated. Vertical movements of the counterweight 10 are brought by the extension and contraction of a lower portion of the main parallel linkage 3.

Figure 2:
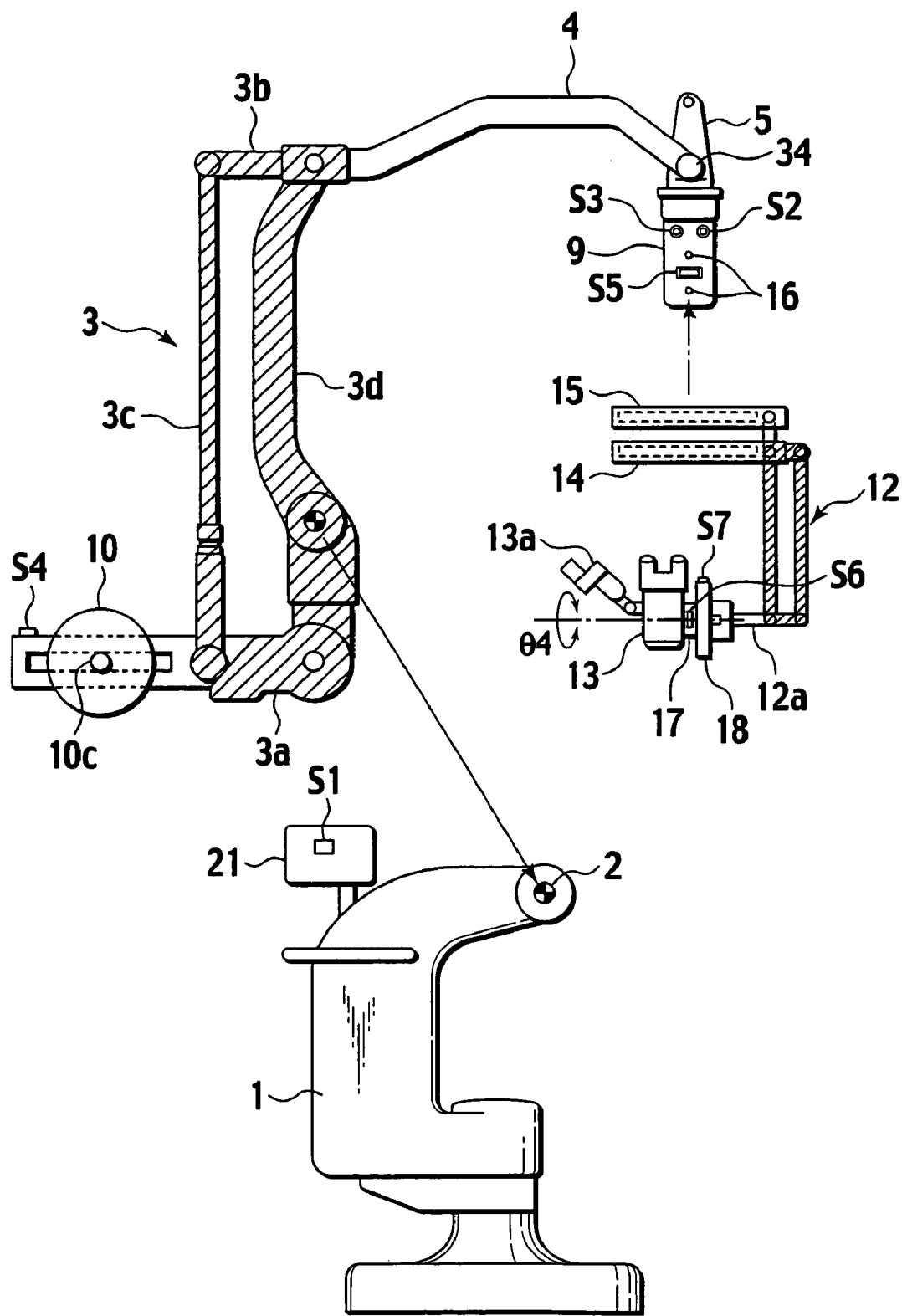
FIG. 2 is an exploded view of the operation microscope stand.

An operation microscope 13 is supported at the distal link 5 via a parallel linkage 12 (see a shaded portion in FIG. 2). The operation microscope 13 is provided with an assistant microscope 13a as an accessory. The parallel linkage 12 is provided with a slide arm 14 being an extension of an upper arm 12b as a link element. An auxiliary parallel linkage 22 (16a-22β-12α-16b) comprises the slide arm 14 and an auxiliary arm 15 in parallel.

The slide arm 14 and the auxiliary arm 15 are engaged with a pair of upper and lower drive axes 16 provided at the slide drive 9, to be slidable and rotatable relative to the drive axes 16, and thereby to constitute a cam mechanism. Accordingly, the slide arm 14 and the auxiliary arm 15 can slide and tilt in parallel to each another with respect to the drive axes 16.

In other words, the parallel linkage 12 and the auxiliary parallel linkage 22 are two parallel linkages being articulated to each other, constituting a supplemental parallel linkage with a link element 16a-16b being fixed relative to the distal link 5. As a result, link elements 16a-22β, 16b-12α, and 12δ (16β)-12γ are parallel to one another, and link elements 16a-16b, 22β (12α)-12δ, and 12β-12γ are parallel to one another. The articulated two parallel linkages define an operating space SP for an operator.

Figure 9:
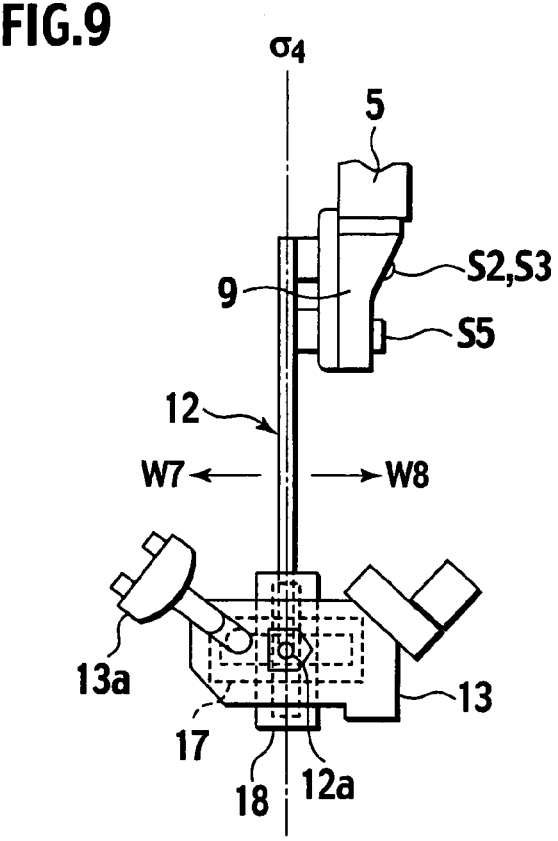
FIG. 9 is a side view illustrating the weight balance of an operation microscope being used.
Figure 10:
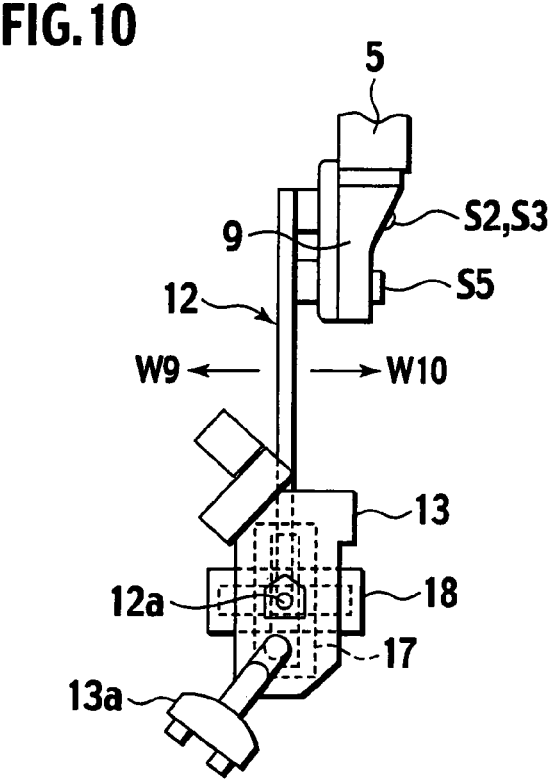
FIG. 10 is a side view illustrating the weight balance of the operation microscope 90° rotated.

The operation microscope 13 is supported at an end of another link element 12a constituting the lower link of the parallel linkage 12 (supplemental parallel linkage), via slide mechanisms 17 and 18 as two-dimensional cam mechanisms (second cam mechanism). The slide mechanisms 17 and 18 are provided in the shape of a cross and can slide in two orthogonal directions. Specifically, the main axes of the slide mechanisms 17 and 18 lie in an imaginary plane which is always normal to the slide arm 14 (the lower link 12a). The main axes of the slide mechanisms 17 and 18 are orthogonal to each other in the imaginary plane. Therefore, weight balancing by the slide mechanisms 17 and 18 and weight balancing by the slide arm 14 can be independently and promptly performed. As shown in FIGS. 9 and 10, the horizontally-oriented one of the slide mechanisms 17 and 18 is slid horizontally for weight balancing.

Referring to FIG. 9, the operation microscope 13 is movable in a horizontal direction along the slide mechanism 17 oriented in a horizontal direction. The slide mechanism 17, together with the operation microscope 13, is movable in a vertical direction along the slide mechanism 18 oriented in a vertical direction. The slide mechanism 18, together with the slide mechanism 17 and the operation microscope 13, is supported rotatably about the lower link 12a relative to the parallel linkage 12 (supplemental parallel linkage).

When weight balancing for the operation microscope 13 is performed in this state, the operation microscope 13 is rotated 90° together with the two slide mechanisms 17 and 18 provided in the cross shape, and one of the slide mechanisms 17 and 18 turned in a horizontal state is moved in a horizontal direction for weight balancing. The reason why the operation microscope 13 is not only directly moved horizontally but also rotated 90° and then moved horizontally is to ensure the weight balance of the operation microscope 13. After rotated 90° and balanced in weight, the operation microscope 13 is returned to an original used state.

Figure 4:
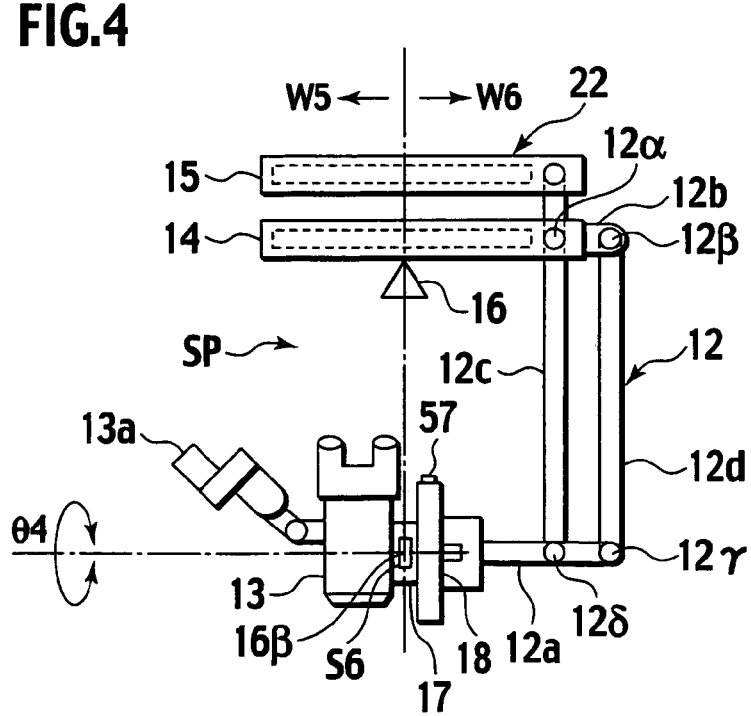
FIG. 4 is a side view illustrating the weight balance of a supplemental parallel linkage.
Figure 5:
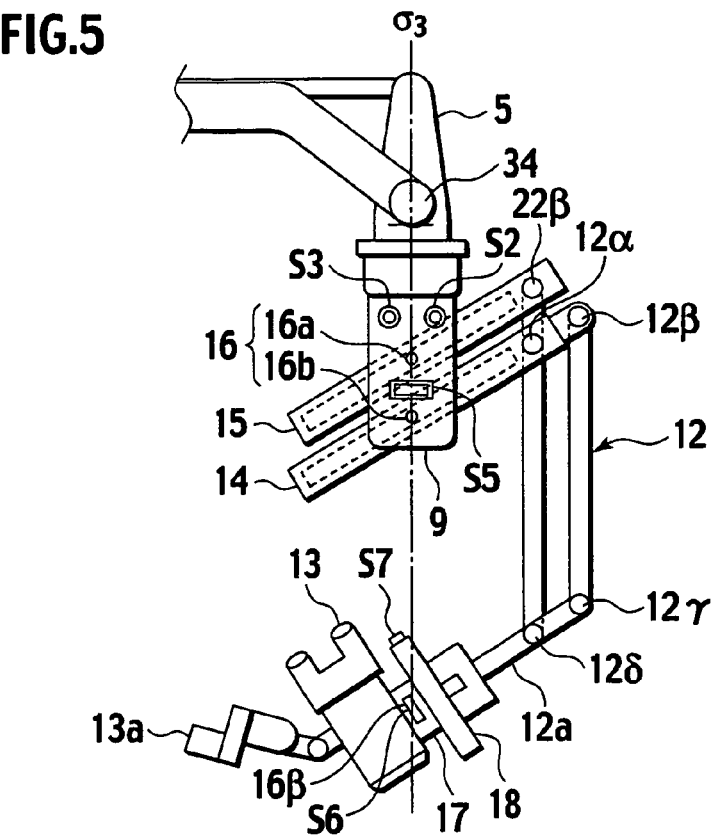
FIG. 5 is a side view of the supplemental parallel linkage inclined to one side.
Figure 6:
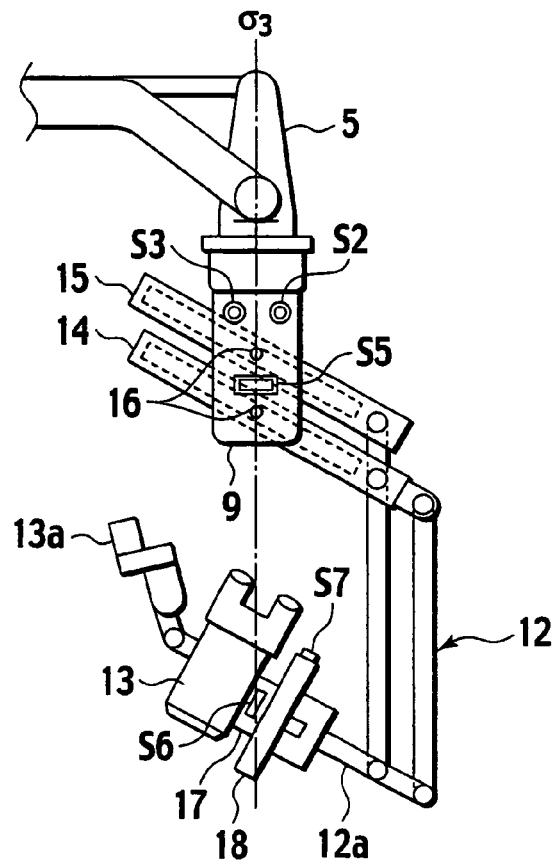
FIG. 6 is a side view of the supplemental parallel linkage inclined to the other side.

As shown in FIG. 4, the slide arm 14 and the auxiliary arm 15 holding the parallel linkage 12 and the operation microscope 13 as a whole are supported on the drive axes 16 of the slide mechanisms 17 and 18. When a weight W5 on the left side on the sheet plane of an imaginary vertical plane passing through the drive axes 16 is balanced with a weight W6 on the right side on the sheet plane, the operation microscope 13 is kept at an optional position in the air. Even when the operation microscope 13 is changed in angle as shown in FIGS. 5 and 6, it is kept in that state (second weight balance). Fulcrums 16, 12α(12β), 12δ(12γ), and 16β constitute the supplemental parallel linkage. A link element 16β-16 is fixed relative to the distal link 5 via the drive axes 16a and 16b. The fulcrum 16 is preferably located in an imaginary vertical plane $\sigma_3$ passing through the rotation axis 34 which is fixed relative to the link element 3b of the main parallel linkage 3. This is because performing an operation for the second weight balance only does not affect the first weight balance. When the second weight balance is attained, the mass center of the load suspended from and supported by the distal link 5 is also located in the imaginary vertical plane $\sigma_3$. As a result, the weight of the load does not substantially generate torque about the rotation axis 34. Thus, a wobble of the operation microscope 13 does not cause the parallel linkages in the stand to fluctuate.

Figure 7:
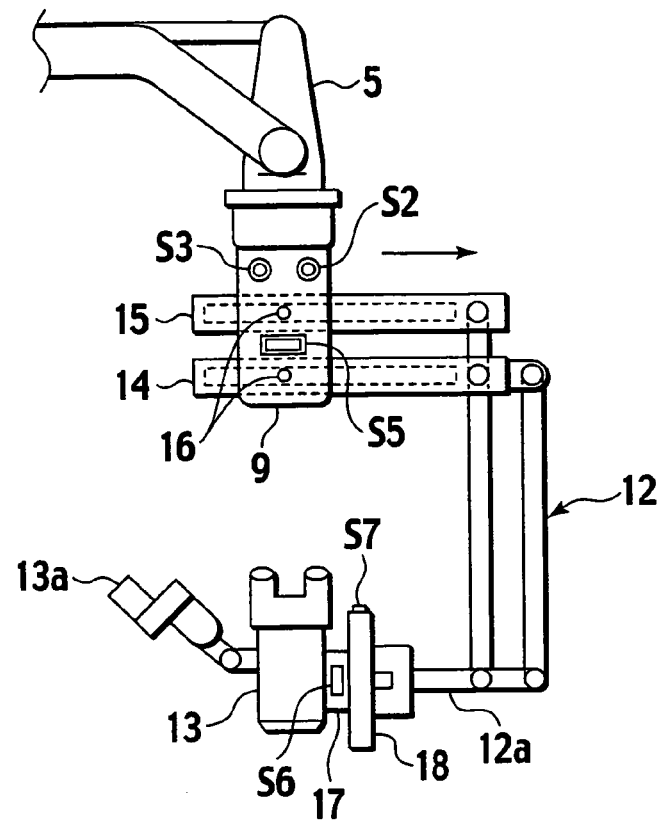
FIG. 7 is a side view of the supplemental parallel linkage slid to one side.
Figure 8:
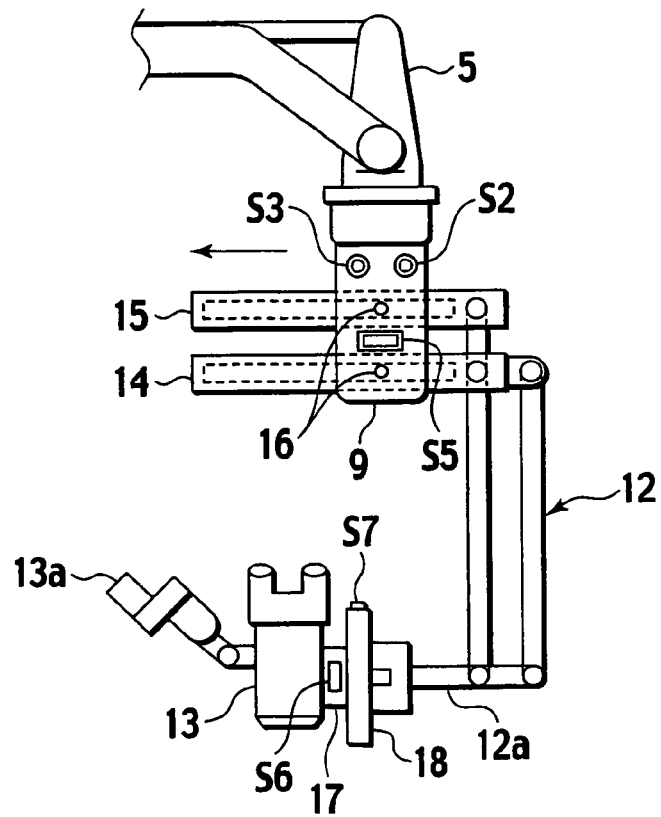
FIG. 8 is a side view of the supplemental parallel linkage slid to the other side.

Even with the parallel linkage 12 and the operation microscope 13 once balanced in weight on the drive axes 16, when an operator changes the orientation of the assistant microscope 13a during surgery, the mass center of the combination of the parallel linkage 12 and the operation microscope 13 can subtly change, preventing the operation microscope 13 from keeping position. To deal with this, the slide drive 9 is controlled by a first slide control means 19. Specifically, in order to balance the weights W5 and W6 on the drive axes 16, as shown in FIGS. 7 and 8, the slide arm 14 and the auxiliary arm 15 are configured to be automatically slid in a weight balancing direction relative to the drive axes 16 and stopped from sliding when balance is attained.

On the other hand, the operation microscope 13, together with the slide mechanisms 17 and 18, is rotatable in $\sigma 4$ directions about the main axis of the lower link 12a of the parallel linkage 12. As shown in FIG. 9, when weights W7 and W8 on opposite sides of an imaginary vertical plane $\sigma_4$ passing through the main axis of the lower link 12a and including a plumb direction are balanced, the mass center of the weights on the opposite sides lies in the imaginary vertical plane $\sigma_4$. Therefore, the operation microscope 13 is kept in position without rotating despite the intention of the operator. Even when rotated about the lower link 12a, the operation microscope 13 is kept in position.

It is necessary for the operation microscope 13 to be balanced in weight even when turned in its entirety. Thus, even when the operation microscope 13 is turned 90° as shown in FIG. 10, weights W9 and W10 on opposite sides of the imaginary vertical plane $\sigma_4$ need to be balanced so as to balance torque about the main axis of the lower link 12a.

Also, as for rotation in the $\theta 4$ directions about the main axis of the lower link 12a, when an operator changes the orientation of the assistant microscope 13a during surgery, the operation microscope 13 is changed in form, and the mass center of the weight subtly shifts. The weight balance of the operation microscope 13 on the lower link 12a thus becomes off-balanced. To deal with this, one of the slide mechanisms 17 and 18 oriented horizontally is controlled by a second slide control means 20.

Figure 11:
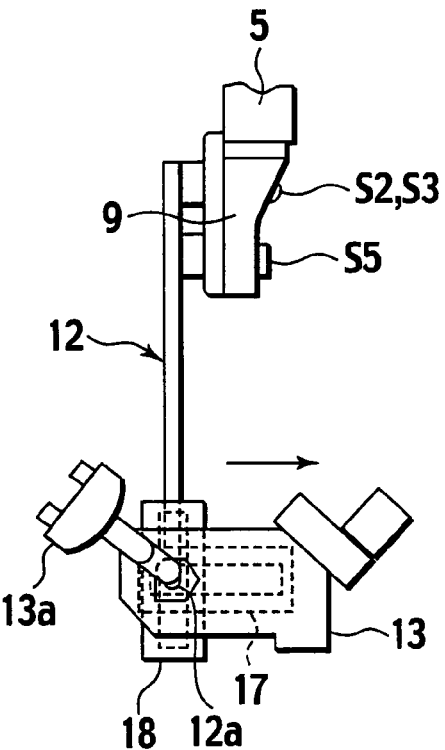
FIG. 11 is a side view of the operation microscope being used, slid to one side.
Figure 12:
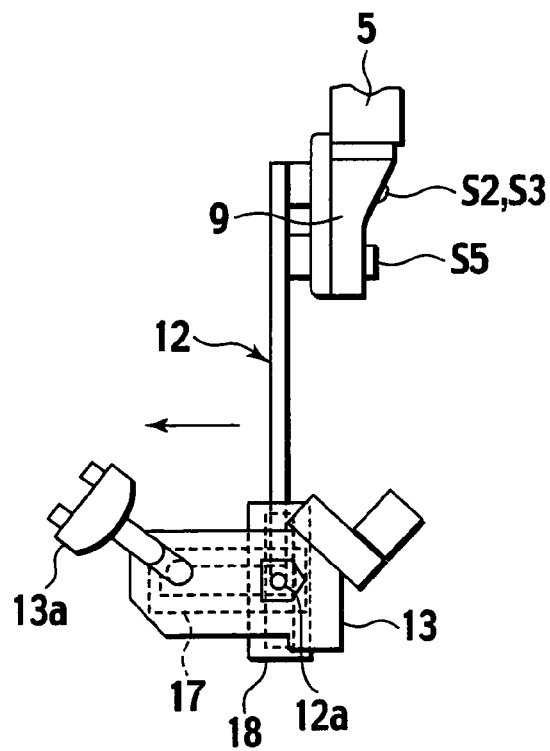
FIG. 12 is a side view of the operation microscope being used, slid to the other side.
Figure 13:
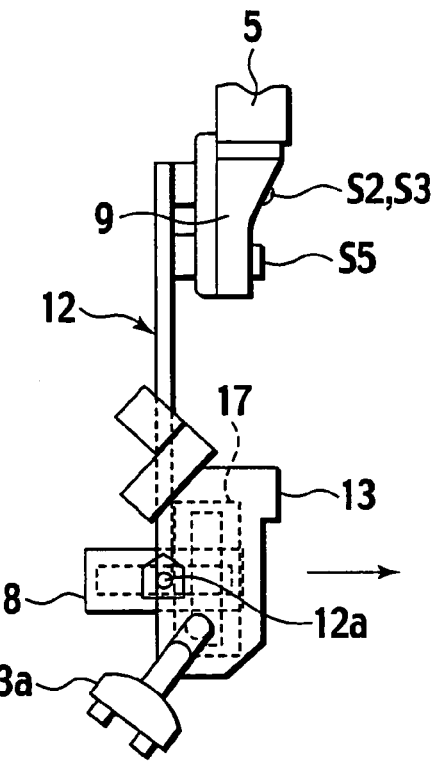
FIG. 13 is a side view of the 90° rotated operation microscope slid to one side.
Figure 14:
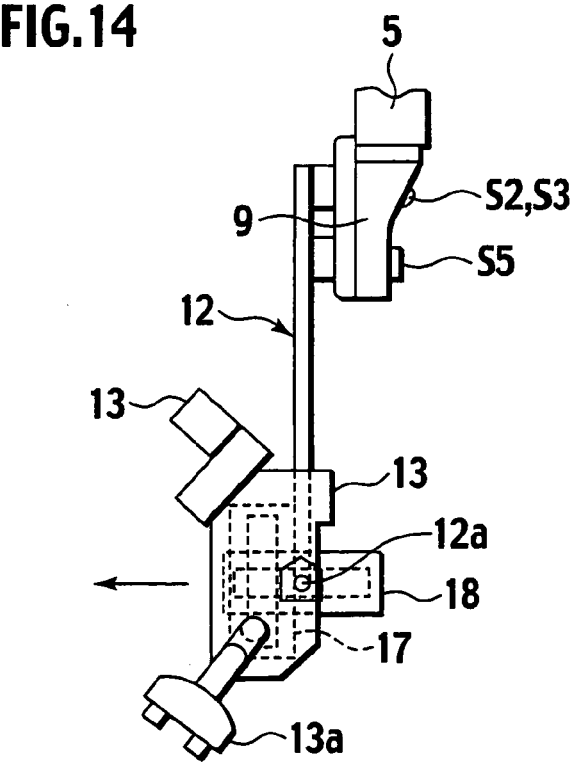
FIG. 14 is a side view of the 90° rotated operation microscope slid to the other side.

Specifically, in order to balance the weights W7 and W8 about the lower link 12a when the operation microscope 13 is used horizontally, as shown in FIGS. 11 and 12, the operation microscope 13 is automatically slid in a weight balancing direction by the slide mechanism 17, the horizontal one of the slide mechanisms 17 and 18, and is stopped sliding when balanced. Also, to balance the weights W9 and W10 in a 90° rotated position, as shown in FIGS. 13 and 14, the operation microscope 13 is slid by the horizontal slide mechanism 18 in a direction to attain weight balance.

A first switch S1 is provided on an operating panel 21 at the stand body 1. With this first switch S1, the counterweight movement control means 11, the first slide control means 19, and the second slide control means 20 are controlled. That is, by pressing the first switch S1, a weight balance of the main parallel linkage 3 about the rotation axis 2, a weight balance of the parallel linkage 12 about the drive axes 16, and a weight balance of the operation microscope 13 about the lower link 12a are all automatically produced. The first switch S1 is pressed to fully adjust all the weight balances before an operation is started.

In addition to the first switch S1, a second switch S2 is provided above the operating space SP defined by the supplemental parallel linkage. More specifically, the second switch 2 is fixed in position at the distal link 5, and is preferably provided at the slide drive 9 which constitutes the lower part of the distal link 5. The second switch S2 only controls the first slide control means 19 and the second slide control means 20 for producing the second weight balance. When the assistant microscope 13a is changed in orientation during surgery, for example, and the weight balance around the operation microscope 13 becomes off-balance, an operator does not press the first switch S1 but presses the second switch S2 at hand.

This is because the weight balance of the main parallel linkage 3 about the rotation axis 2 is not disrupted, and only the weight balance of the parallel linkage 12 about the drive axes 16 and the weight balance of the operation microscope 13 in the $\theta 4$ direction about the lower link 12a are disrupted. Thus, only by pressing the second switch S2, the weight balance around the operation microscope 13 can be adjusted in a short period of time. Also, since the second switch S2 is provided at the lower part of the distal link 5 which is near the operation microscope 13, it is easy for an operator to press the second switch S2 during surgery.

The first weight balance and the second weight balance can be maintained only through an operation for the second weight balance by an operation of the second switch S2 because the second weight balance and the first weight balance can be independently controlled as described above.

A third switch S3 connected only to the counterweight movement control means 11 is also provided at the slide drive 9 as the lower part of the distal link 5. After a weight balance is attained by the counterweight movement control means 11, the counterweight 10 can come into contact with a sterile drape entirely covering the stand, for example, thereby slightly disrupting the weight balanced state of the main parallel linkage 3. In such a case, an operator does not press the first switch S1 but presses the third switch S3 at hand. Since the third switch S3 is also provided at the slide drive 9 which is close to the operation microscope 13, it is easy for the operator to press it during surgery.

A manual switch S4 for moving the counterweight 10 is provided near the counterweight 10. A manual switch S5 for sliding the slide arm 14 and the auxiliary arm 15 is provided at the slide drive 9. Manual switches S6 and S7 for sliding the two slide mechanisms 17 and 18 are also provided thereto, respectively. These manual switches S4 through S7 can be pressed at either end thereof, and are configured to slide the corresponding components in the direction of the pressed end by a predetermined distance. Therefore, even if the first switch S1, the second switch S2 and the third switch S3 fail, an operator can use the manual switches S4 through S7 for attaining weight balances of the corresponding parts.

As an accessory of the operation microscope 13, a video camera, an opposed lens-barrel or the like can be mounted thereto in addition to the assistant microscope 13a.

According to the present invention, the first switch S1 for performing both a weight balancing operation for the main parallel linkage 3 and a weight balancing operation for the supplemental parallel linkage 12, 22 is provided separately from the second switch S2 for only performing a weight balancing operation for the supplemental parallel linkage 12, 22. Therefore, an operator can only correct a slight unbalanced state of the supplemental parallel linkage 12, 22 in a short period of time by pressing the second switch S2 during surgery, resulting in increased operability of the operation microscope 13.

Also, the supplemental parallel linkage 12, 22 supporting the operation microscope 13 can be slid to attain the weight balance of the supplemental parallel linkage 12, 22 with respect to the drive axes 16 at the distal link 5, and the operation microscope 13 can be slid to attain the weight balance of the operation microscope 13 about the lower link 12a of the parallel linkage 12. Thus, the unbalanced state of the supplemental parallel linkage 12, 22 can be corrected independently in a more reliable manner.

This application claims benefit of priority under 35 USC §119 to Japanese Patent Applications No. 2004-131790, filed on Apr. 27, 2004, the entire contents of which are incorporated by reference herein. Although the invention has been described above by reference to certain embodiments of the invention, the invention is not limited to the embodiments described above. Modifications and variations of the embodiments described above will occur to those skilled in the art, in light of these teachings. The scope of the invention is defined with reference to the following claims.

What is claimed is:

1. A weight balancing mechanism for a stand supporting an operation microscope, comprising:
    a first parallel linkage being supported on a first rotation axis which is fixed relative to a stand body;
    a distal link being supported on a second rotation axis which is fixed relative to a first horizontal link element of the first parallel linkage;
    a second parallel linkage being supported on a third rotation axis which is fixed relative to the distal link, and an operation microscope being suspended from and supported by the third rotation axis via the second parallel linkage;
    a counterweight being fixed relative to a second horizontal link element of the first parallel linkage, on the side opposite to the distal link with respect to the first rotation axis;
    a first control mechanism configured to produce a first weight balance about the first rotation axis for the first parallel linkage by using the counterweight;
    a second control mechanism configured to produce a second weight balance about the third rotation axis for the second parallel linkage;
    a first switch controlling an operation of the first control mechanism and the second control mechanism; and
    a second switch controlling only an operation of the second control mechanism; wherein,
    the second parallel linkage defines an operating space; and
    the second switch is located above the operating space.

2. A weight balancing mechanism according to claim 1, wherein the second switch is fixed relative to the distal link.

3. A weight balancing mechanism according to claim 1, wherein:
    the second parallel linkage comprises a first vertical link element, a first horizontal link element, a second vertical link element, and a second horizontal link element;
    the first vertical link element of the second parallel linkage is fixed relative to the distal link; and
    the operation microscope is fixed relative to the second horizontal link element of the second parallel linkage.

4. A weight balancing mechanism according to claim 3, wherein:
    the counterweight can be moved to a position to produce the first weight balance by the first control mechanism; and
    the operation microscope is movable relative to the second horizontal link element of the second parallel linkage by the second control mechanism.

5. A weight balancing mechanism according to claim 4, wherein the mass center of the operation microscope and the second parallel linkage being suspended from and supported by the distal link is controlled to position substantially in the direction of gravity with respect to the third rotation axis by the second control mechanism according to an operation of the second switch.

6. A weight balancing mechanism according to claim 5, wherein the third rotation axis is positioned substantially in the direction of gravity with respect to the second rotation axis.

7. A weight balancing mechanism according to claim 1, wherein:
    the second parallel linkage comprises a first auxiliary parallel linkage and a second auxiliary parallel linkage, the first auxiliary parallel linkage and the second auxiliary parallel linkage being articulated to each other, having link elements parallel to each another;
    the first auxiliary parallel linkage is fixed relative to the distal link via articulations being fixed relative to a link element thereof, the articulations being provided with a first cam mechanism being controlled by the second control mechanism;
    the operation microscope is fixed relative to a horizontal link element of the second auxiliary parallel linkage via a second cam mechanism being controlled by the second control mechanism in which the horizontal link element is not parallel to the distal link element;
    the counterweight is movable to a position in order to produce the first weight balance by the first control mechanism; and
    the mass center of the operation microscope and the second parallel linkage being suspended from and supported by the distal link is controlled to position substantially in the direction of gravity with respect to the third rotation axis by the second control mechanism according to an operation of the second switch.

8. A weight balancing mechanism according to claim 7, wherein the second control mechanism controls the second cam mechanism to balance the weight of the operation microscope and controls the first cam mechanism to balance the weight of the second parallel linkage, according to the operation of the second switch.

9. A weight balancing mechanism according to claim 7, wherein the third rotation axis is positioned substantially in the direction of gravity with respect to the second rotation axis.

10. A weight balancing mechanism according to claim 8, wherein:
    the second cam mechanism includes a first slide mechanism to slide in a first direction perpendicular to the horizontal link element, and a second slide mechanism to slide in a second direction orthogonal to the horizontal link element and the first direction; and
    the second control mechanism produces the second weight balance in a position where the first direction is oriented horizontally, and also produces the second weight balance in a position where the second direction is oriented horizontally.

11. A weight balancing mechanism according to claim 1, further comprising a third switch for only controlling operation of the first control mechanism, the third switch being located above the operating space.

* * * * *